(12) United States Patent
Op De Beeck et al.

(10) Patent No.: US 10,271,796 B2
(45) Date of Patent: Apr. 30, 2019

(54) BIOCOMPATIBLE PACKAGING

(71) Applicant: IMEC, Leuven (BE)

(72) Inventors: Maria Op De Beeck, Leuven (BE); Eric Beyne, Leuven (BE); Philippe Soussan, Marseilles (FR)

(73) Assignee: IMEC, Leuven (BE)

( * ) Notice: Subject to any disclaimer, the term of this patent is extended or adjusted under 35 U.S.C. 154(b) by 48 days.

(21) Appl. No.: 14/696,223

(22) Filed: Apr. 24, 2015

(65) Prior Publication Data

US 2015/0297136 A1 Oct. 22, 2015

Related U.S. Application Data

(63) Continuation of application No. 13/333,836, filed on Dec. 21, 2011, now Pat. No. 9,048,198, which is a
(Continued)

(51) Int. Cl.
*H01L 23/31* (2006.01)
*A61B 5/00* (2006.01)
(Continued)

(52) U.S. Cl.
CPC ......... *A61B 5/686* (2013.01); *A61M 5/14276* (2013.01); *A61N 1/375* (2013.01); *A61N 1/37205* (2013.01); *H01L 23/3114* (2013.01); *A61B 5/6861* (2013.01); *A61B 2562/028* (2013.01); *A61B 2562/0247* (2013.01); *A61M 2205/0244* (2013.01); *A61M 2205/8206* (2013.01); *A61N 1/3756* (2013.01); *H01L 24/48* (2013.01); *H01L 2224/451* (2013.01);
(Continued)

(58) Field of Classification Search
CPC .............................. H01L 23/28; H01L 23/291
USPC ................ 438/127, 114, 113, 464, 465, 462; 257/E21.602
See application file for complete search history.

(56) References Cited

U.S. PATENT DOCUMENTS 6,063,696 A 5/2000 Brenner et al.
6,379,999 B1 4/2002 Tanabe
(Continued)

FOREIGN PATENT DOCUMENTS

EP 0818808 A2 1/1998

OTHER PUBLICATIONS

International Search Report for International application No. PCT/EP2010/059055 dated Mar. 3, 2011 by European Patent Office.

*Primary Examiner* — Andres Munoz
(74) *Attorney, Agent, or Firm* — Knobbe Martens Olson & Bear LLP

(57) ABSTRACT

A method is disclosed for packaging a device, e.g., for bio-medical applications. In one aspect, the method includes obtaining a component on a substrate and separating the component and a first part of the substrate from a second part of the substrate using at least one physical process inducing at least one sloped side wall on the first part of the substrate. The method also includes providing an encapsulation for the chip. The resulting packaged chip advantageously has a good step coverage resulting in a good hermeticity, less sharp edges resulting in a reduced risk of damaging or infection after implantation and has a relatively small packaged volume compared to conventional big box packaging techniques.

12 Claims, 11 Drawing Sheets

Related U.S. Application Data continuation of application No. PCT/EP2010/059055, filed on Jun. 25, 2010.

(60) Provisional application No. 61/220,528, filed on Jun. 25, 2009.

(51) Int. Cl.
*A61N 1/375* (2006.01)
*A61N 1/372* (2006.01)
*A61M 5/142* (2006.01)
*H01L 23/00* (2006.01)

(52) U.S. Cl.
CPC ............. *H01L 2224/48227* (2013.01); *H01L 2924/00014* (2013.01); *H01L 2924/10253* (2013.01); *H01L 2924/14* (2013.01); *H01L 2924/1461* (2013.01); *H01L 2924/181* (2013.01)

(56) References Cited

U.S. PATENT DOCUMENTS

| | | | |
|---|---|---|---|
| 6,953,560 B1 * | 10/2005 | Castro | A61F 2/82 |
| | | | 423/423 |
| 7,371,693 B2 | 5/2008 | Suzuki et al. | |
| 7,632,307 B2 * | 12/2009 | Pacetti | A61L 31/10 |
| | | | 623/1.44 |
| 9,048,198 B2 | 6/2015 | Op De Beeck et al. | |
| 2002/0197877 A1 | 12/2002 | Arita et al. | |
| 2003/0078484 A1 * | 4/2003 | Schulman | A61B 5/14532 |
| | | | 600/373 |
| 2003/0216010 A1 | 11/2003 | Atlas | |
| 2004/0142509 A1 | 7/2004 | Imai | |
| 2005/0067186 A1 | 3/2005 | Mizutani | |
| 2005/0167799 A1 | 8/2005 | Doan | |
| 2006/0030127 A1 | 2/2006 | Fukasawa et al. | |
| 2007/0010702 A1 * | 1/2007 | Wang | A61F 2/82 |
| | | | 600/8 |
| 2007/0088442 A1 * | 4/2007 | Cima | A61B 5/055 |
| | | | 623/18.11 |
| 2007/0111353 A1 | 5/2007 | McCaskill et al. | |
| 2008/0315407 A1 | 12/2008 | Andrews, Jr. et al. | |
| 2008/0315434 A1 | 12/2008 | McElrea et al. | |
| 2009/0186465 A1 | 7/2009 | Fujisawa et al. | |
| 2012/0165888 A1 * | 6/2012 | Libbus | A61N 1/36117 |
| | | | 607/18 |

* cited by examiner (a)

(b)

(c)

BIOCOMPATIBLE PACKAGING

CROSS REFERENCE TO RELATED APPLICATIONS

This application is a continuation of U.S. patent application Ser. No. 13/333,836, filed Dec. 21, 2011, which is a continuation of PCT Application No. PCT/EP2010/059055, filed Jun. 25, 2010, which claims priority under 35 U.S.C. § 119(e) to U.S. Provisional Patent Application No. 61/220,528 filed on Jun. 25, 2009. Each of the above applications is incorporated herein by reference in its entirety.

BACKGROUND OF THE INVENTION

Field of the Invention

The disclosed technology relates to the field of bio-medical applications, and more particularly, to the present invention relates to packaging methods for components, such as chips, for bio-medical in vivo applications and packaged devices thus obtained.

Description of the Related Technology

Implantable chips are used in bio-medical in vivo applications e.g. for performing controlling or monitoring functions. Such implantable chips should be packaged to protect the body from leakage of harmful products from the chip towards the body, or from other harmful influences such as mechanical friction of the implanted chip in the body. Furthermore, the chip should be protected from influences from the body, such as diffusion from bio-products from the body into the chip, resulting in damaging or improper functioning of the chip.

A known way of packaging chips for medical applications takes care of the required bi-directional protection, by placing the chip in a 'big box', often a Titanium housing surrounding a chip mounted on a printed circuit board PCB. In this known way of packaging, the package is large in comparison with the size of the original chip, requiring larger incisions during implantation, thus resulting in a more extensive wound healing and inflammation process. Furthermore, the larger the implant, the larger the fibrous encapsulation may be resulting in a higher risk on local tissue irritation for the patient during the lifetime of the implant. When applying the 'big box' packaging technique, the chip itself often also is packaged with an individual standard package, before it is mounted on the PCB.

By way of illustration, cross sectional views of two types of conventional chip packages are shown. In a first example in FIG. 1a, a chip 100 having an individual package 110 is shown whereby metal wires 120 are provided for connecting the individually packaged chip to the PCB 130. The device is furthermore packed completely in a device housing 140. As the standard individual chip packaging is not bio-compatible, the second packaging, referred to as the device housing 140 here definitely is required resulting in a much higher total packaging cost. In FIG. 1b, packaging of a chip 100 that is mounted directly on the PCB whereby only a single packaging is present, being the device housing 140. In this case the chip is not packaged individually and there is a risk of chip contamination or damage, resulting in device malfunctioning. The individual packaging of chips as illustrated by FIG. 1a, has the disadvantage of being a time consuming and expensive process, as all chips conventionally are packaged individually.

U.S. Pat. No. 7,371,693 B2 describes a glass-based device wherein chip sized packaging is performed by separation of individual dies using wet etching of a groove between dies. The wet etching furthermore has a rounding effect for the sharp edges of the dies. The document furthermore describes the provision of a protection film. The protection film is not provided to hermetically encapsulate the device

SUMMARY OF CERTAIN INVENTIVE ASPECTS

Certain inventive aspects relate to good methods and systems for packaging devices e.g. for bio- or bio-medical-applications and packaged devices thus obtained. It is an advantage of one inventive aspect that the packaged devices can be small, e.g. substantially of a similar size as or only slightly larger than the original device size itself. It is an advantage of one inventive aspect that a biocompatible device, e.g. a biocompatible chip, can be obtained, that is provided with a reliable diffusion barrier. It is an advantage of one inventive aspect that a safe solution for preventing diffusion can be obtained. The latter can amongst others be obtained by providing a device encapsulation composed out of stacked layers fully encapsulating the device, at least one of the layers being made of a bio-compatible material.

It is an advantage of one inventive aspect that the packaging method can be applied to substrates comprising a plurality of components, e.g. full semiconductor wafers with a plurality of dies, so that part of the encapsulation process in the packaging process can be performed simultaneously for the plurality of components. The latter results in a decrease in cost and effort, e.g. in a cheaper production process, especially for chip fabrication, as a large number of dies may be present on a substrate.

It is an advantage of one inventive aspect that at least part of the encapsulation can be performed in a clean environment, e.g. in clean room conditions after chip processing, and that in this way contamination and/or damage can be avoided. The latter is possible as providing the encapsulation is performed with conventional clean-room deposition or coating techniques.

It is an advantage of one inventive aspect that good step coverage can be obtained for the encapsulation resulting in uniform thickness of the encapsulation, assisting in obtaining a reliable diffusion barrier. It furthermore is an advantage that good step coverage can be obtained even when using low temperature deposition processes.

It is an advantage of one inventive aspect that a packaged device with smooth edges can be obtained, thus decreasing the risk on local tissue irritation upon implantation of the device.

It is an advantage of one inventive aspect that one or more of these advantages can be obtained in combination with a packaging technique that is substantially material independent, i.e. independent of the substrate or component materials used.

One inventive aspect relates to a method for packaging a device, the method comprising obtaining a component on a substrate, separating the component and a first part of the substrate from a second part of the substrate using at least one physical process inducing at least one sloped side wall on the first part of the substrate, and providing an encapsulation for the component. With sloped side wall reference may be made to a side wall that is oriented not perpendicular to the substrate surface. It is an advantage of one inventive aspect that packaged devices can be obtained that are suitable for bio-medical applications. It is an advantage of one inventive aspect that the packaged devices may induce little or no irritation because sharp edges are avoided in the packaged device. It thereby is an advantage of one inventive aspect that the packaging method can be applied substantially independent of the materials used in the chip or as substrate. In this way, such packaging may be used for substantially all types of chip materials and/or all types of substrate materials. It is an advantage of one inventive aspect that a good step coverage of the encapsulation can be obtained. Using the at least one physical process may comprise at least dicing using a blade with substantially sloped blade surfaces so as to create a recess or cut with sloped side walls. It is an advantage of one inventive aspect that a simple mechanical technique can be applied for performing the separating process. Alternatively, the physical process may include for example laser cutting. Generating the sloped blade surface may then be obtained by controlling the laser beam profile or laser beam orientation.

Separating may comprise using a physical process inducing a sloped surface in the first part of the substrate at the side of the substrate where the component is present on the substrate.

Separating and providing an encapsulation may comprise providing a recess in a top surface of the substrate using the at least one physical process inducing at least one sloped side wall so that the recess comprises at least one sloped side wall, and depositing a first capping layer covering a top surface of the substrate and at least part of the recess. It is an advantage of one inventive aspect that part of the encapsulation, i.e. the provision of the first capping layer, can be performed to the full substrate which may comprise a plurality of chips, thus allowing part of the encapsulation process to be performed simultaneously and efficiently for a plurality of chips. It is an advantage of one inventive aspect that a good coverage can be obtained by the capping layers.

Providing a recess in a top surface of the substrate may comprise applying a first dicing process to the top surface with a blade providing a cut with side walls substantially perpendicular to the substrate top surface, and applying at least one second dicing process to the top surface with a blade providing a cut with sloped side walls substantially non-perpendicular to a surface of the substrate, the first dicing process and the second dicing process being performed at substantially the same location on the substrate surface. It is an advantage of one inventive aspect that the double dicing technique allows to make the edges of the packaged chip less sharp, resulting in reduction of irritation or damaging of tissue after implantation.

Separating may comprise using a second physical process inducing a sloped surface in the first part of the substrate at the side of the substrate opposite to the side of the substrate where the component is present on the substrate. It is an advantage of one inventive aspect that a packaging can be obtained whereby all corners of the packaged chip can be rounded.

Separating and providing an encapsulation furthermore may comprise thinning the bottom surface of the substrate, e.g. at least at a position substantially opposite to the recess at the top surface of the substrate, so that a cut is formed and the first part of the substrate is separated from the second part of the substrate, and depositing a first capping layer covering the bottom surface and at least part of the area corresponding with the walls of the cut at the bottom surface of the substrate. In one inventive aspect, the provision of the recess at the bottom surface of the substrate may be made using any suitable technique. It is an advantage of one inventive aspect that a good coverage can be obtained by the capping layers.

After thinning the bottom surface of the substrate, the method may comprise using a second physical process inducing at least one sloped side wall so that the edge at the bottom surface comprises a sloped side wall. In one inventive aspect, all corners of the resulting encapsulated chip can be less sharp or unsharp, i.e. corners being substantially less sharp than about 90°, resulting in a reduced risk of irritation after implantation.

For thinning the bottom surface of the substrate, the substrate may be fixed with the top surface to a carrier before thinning and the carrier may be removed after inducing at least one sloped side wall at the bottom surface. It is an advantage of one inventive aspect that at least part of the packaging process can be performed simultaneously for a plurality of chips so that the number of steps in the packaging process involving individual handling of chips can be reduced.

The method furthermore may comprise providing a further encapsulation layer after the separating. It is an advantage of one inventive aspect that encapsulation can be formed from at least two layers, allowing an encapsulated chip with limited size, i.e. only slightly larger than the chip integrated on the substrate. It is an advantage of one inventive aspect that a good coverage and hermiticity can be obtained.

Prior to providing a further encapsulation layer, an additional cleaning step may be performed.

The method may comprise applying a protective top coating for protecting the chip before using the at least one physical process inducing a sloped surface.

The method may comprise applying a plasma treatment for removing surface damage after using the at least one physical process inducing a sloped surface.

The method may comprise applying a plasma treatment for removal of surface damage after the thinning of the wafer. Providing an encapsulation for a component may comprise depositing an encapsulation layer using two subsequent and distinct depositions of sub-layers, the sub-layers forming the encapsulation layer. It is an advantage of one inventive aspect that the number of pinholes throughout the full encapsulation layer can be reduced.

One inventive aspect relates to a device for bio-medical applications, the device comprising a component present on a substrate, wherein the device comprises at least one sloped side wall induced using a physical process.

One inventive aspect relates to a device for bio-medical applications, the device comprising a component on a substrate, the device having a hermetic bio-compatible packaging comprising a first capping layer and a further encapsulation layer. It is an advantage of one inventive aspect that packaged devices can be obtained with a good coverage by the encapsulation material and with a hermetic packaging, thus avoiding diffusion from and towards the device after implantation. The bio-compatible packaging may consist of the first capping layer and the further encapsulation layer. It is an advantage of one inventive aspect that packaged devices can be obtained whereby good packaging is obtained using only two encapsulation layers, making the packaging technique relatively efficient. It is an advantage of one inventive aspect that hermetic packaging is obtained for individual dies.

The first capping layer and the further encapsulation layer may be positioned in solid contact with the component on the substrate. It is an advantage of one inventive aspect that packaged devices can be obtained that are only slightly larger than the chip integrated on the substrate itself. With solid contact reference may be made to direct contact with the chip integrated on the substrate or to indirect contact whereby only solid materials, e.g. other layers, are present in between. The packaging may be provided as a stack of layers.

One inventive aspect relates to a biocompatible system, the biocompatible system comprising at least one packaged device as described above. The biocompatible system may comprise at least two packaged devices and a global encapsulation.

One inventive aspect relates to a method for packaging a device, the method comprising obtaining a component present on a substrate and providing a hermetic bio-compatible packaging by providing a first capping layer and a further encapsulation layer in solid contact with the component present on the substrate. Providing a first capping layer may comprise providing at least part of a first capping layer before cutting the chip integrated on a first part of the substrate from a remainder part of the substrate.

In some embodiments, bi-directional diffusion barrier are obtained whereby no leaching of bodily fluids into the implant occurs, and no diffusion of harmful components of the implant into tissue occurs. It is furthermore an advantage of one inventive aspect that the devices can remain functional after packaging and after implantation.

Certain inventive aspects are set out in the accompanying independent and dependent claims. Features from the dependent claims may be combined with features of the independent claims and with features of other dependent claims as appropriate and not merely as explicitly set out in the claims.

The improvements in the packaging methods provided by certain inventive aspects result in better and/or more reliable bio-medical implantable devices.

Certain embodiments of the invention will now further be discussed in the detailed description in conjunction with the drawings. The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF CERTAIN ILLUSTRATIVE EMBODIMENTS

Figure 1A:
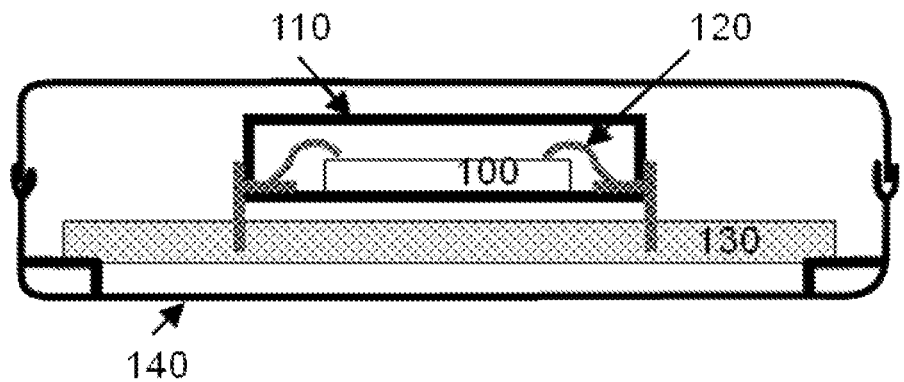
FIG. 1a and FIG. 1b illustrates two cross sectional views of chip packages for implantable chips as known from prior art.
Figure 1B:
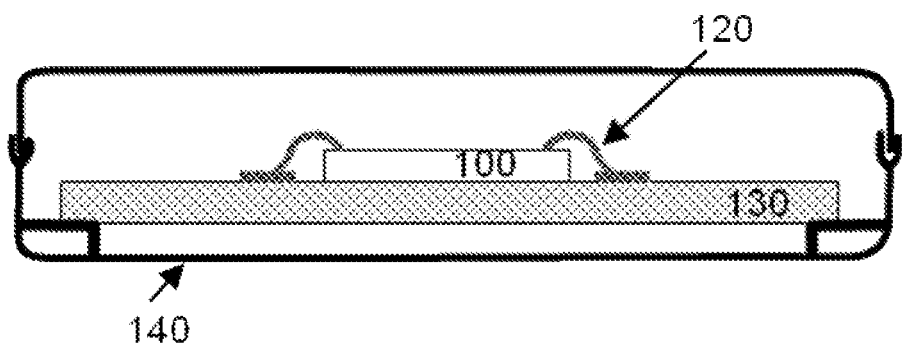

In the following detailed description, numerous specific details are set forth in order to provide a thorough understanding of the invention and how it may be practiced in particular embodiments. However it will be understood that the present invention may be practiced without these specific details. In other instances, well-known methods, procedures and techniques have not been described in detail, so as not to obscure the present invention. While the present invention will be described with respect to particular embodiments and with reference to certain drawings, the reference is not limited hereto.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein. For example, it is to be noticed that the step of separating and of providing an encapsulation may be interchanged in order or may comprise a number of sub-steps that intermix with each other, i.e. the order of the steps may be interchanged, the order of the sub-steps within one step may be interchanged or the order of the sub-steps within different steps may be interchanged as appropriate. In the following description, by way of illustration, a number of examples and embodiments with interchanged steps will be discussed, the present invention not being limited thereto.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the steps or elements listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B. Where reference is made to the term consists of, the latter implies that no other elements are present.

Where in certain embodiments of the present invention reference is made to biocompatible, reference is made to the ability of a medical device to perform its intended function, with the desired degree of incorporation in the host without eliciting any undesirable local or systemic effects in that host. The medical device thereby may be positioned in the host with reduced or minimal interaction that adversely affects device. The biocompatibility demands will depend on the type of contact between the medical device and the host, the position of the implant and the period the implantable device will stay in the host.

In a first aspect, there is a method for packaging a device. The device thereby typically may be a component on a substrate. One type of such components may be integrated circuits, also referred to as dies, including the back-end-of-line process. Another example of such components may be micro electromechanical systems (MEMS), including 0-th level packaged MEMS, thin film capped MEMS, etc. The MEMS devices may for example be passive components, actuators, sensors, etc. A further example of such components may be micro-fluidics devices. Still another example is a battery, e.g. a battery integrated in silicon, e.g. a rechargeable battery. The substrate may be any suitable substrate such as for example a semiconductor substrate, e.g. a silicon substrate, an electrically insulating substrate, a glass substrate, a polymer substrate, and where allowable an electrically conducting substrate such as for example a metal. The method is especially suitable for packaging of devices, such as e.g. chips, for bio-medical applications, e.g. for making implantable devices for in-vivo applications. The method according to one embodiment comprises obtaining a component on a substrate. The latter may include manufacturing such a component on a substrate, as can be done using conventional techniques, or obtaining such components on a substrate from the shelve. The method furthermore comprises separating the component and a first part of the substrate from a second, remainder, part of the substrate using at least one physical process thus inducing at least one sloped side wall on the first part of the substrate. A sloped side wall thereby may be a wall or part thereof being non-perpendicular to the top surface of the substrate. Such physical processes may include dicing, laser cutting, etc. The presence of sloped side walls will result in less sharp edges in the packaged device, such that there is less risk on injury or irritation upon and after implantation. The packaged device may be part of a larger system in which a number of devices are grouped, optionally electrically connected, as will be described further. The larger system may be packaged using a second packaging. In such cases, less sharp edges of the packaged device also may result in an increased reliability of the second packaging for the larger system. The method also comprises providing an encapsulation for the component and the first part of the substrate. The encapsulation can be composed out of one or more levels of packaging. According to one embodiment, these levels of packaging consist out of layers of materials, e.g. bio-compatible materials. Typical materials that could be used for packaging, as single layer or stack of layers, may include polyurethane, polycarbonate urethane, silicone, silicone-polyester-urethane, polyimide, durimide (photo-definable polyimide), parylene, cyclic olefin polymer (COP), cyclic olefin copolymer (COC), polymethyl methacrylate (PMMA), polyether ether ketone (PEK), polyphenylene, polysulfone, polyphenylsulfone, embodiments of the present invention not being limited hereto. Although in the present illustration the example is given by a packaging of two levels, the present invention is not limited thereto and more packaging levels may be added. The use of several stacked layers as packaging can be a safe solution to ensure total encapsulation and to obtain a reliable diffusion barrier. Embodiments using stacked layer encapsulation results in smaller packaged devices, which results in easier wound healing and less risk on local tissue irritation upon implantation. As indicated above, separating and providing an encapsulation may be intermixed.

Figure 2:
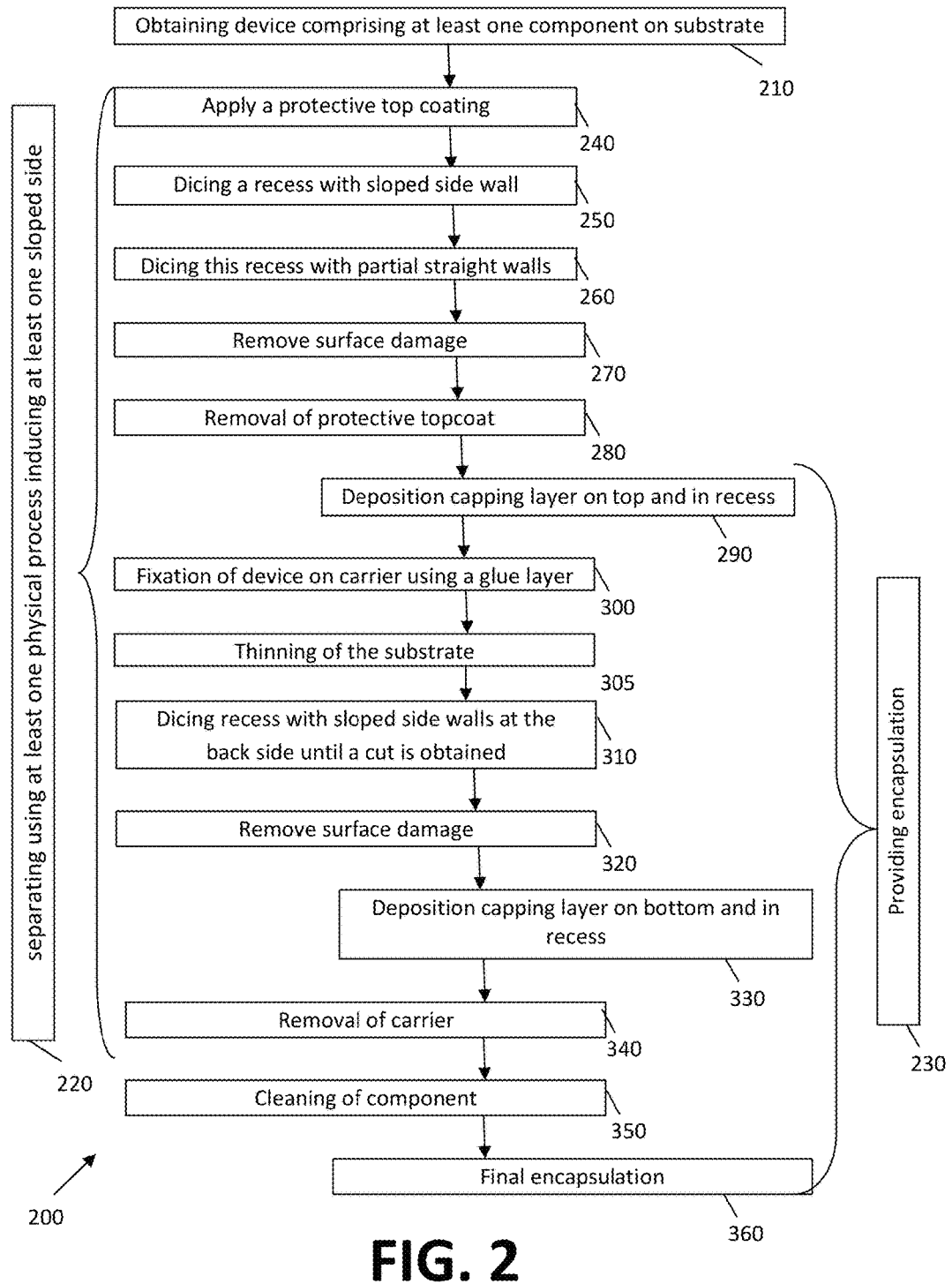
FIG. 2 illustrates an exemplary flow chart for a packaging method according to one embodiment.
Figure 3:
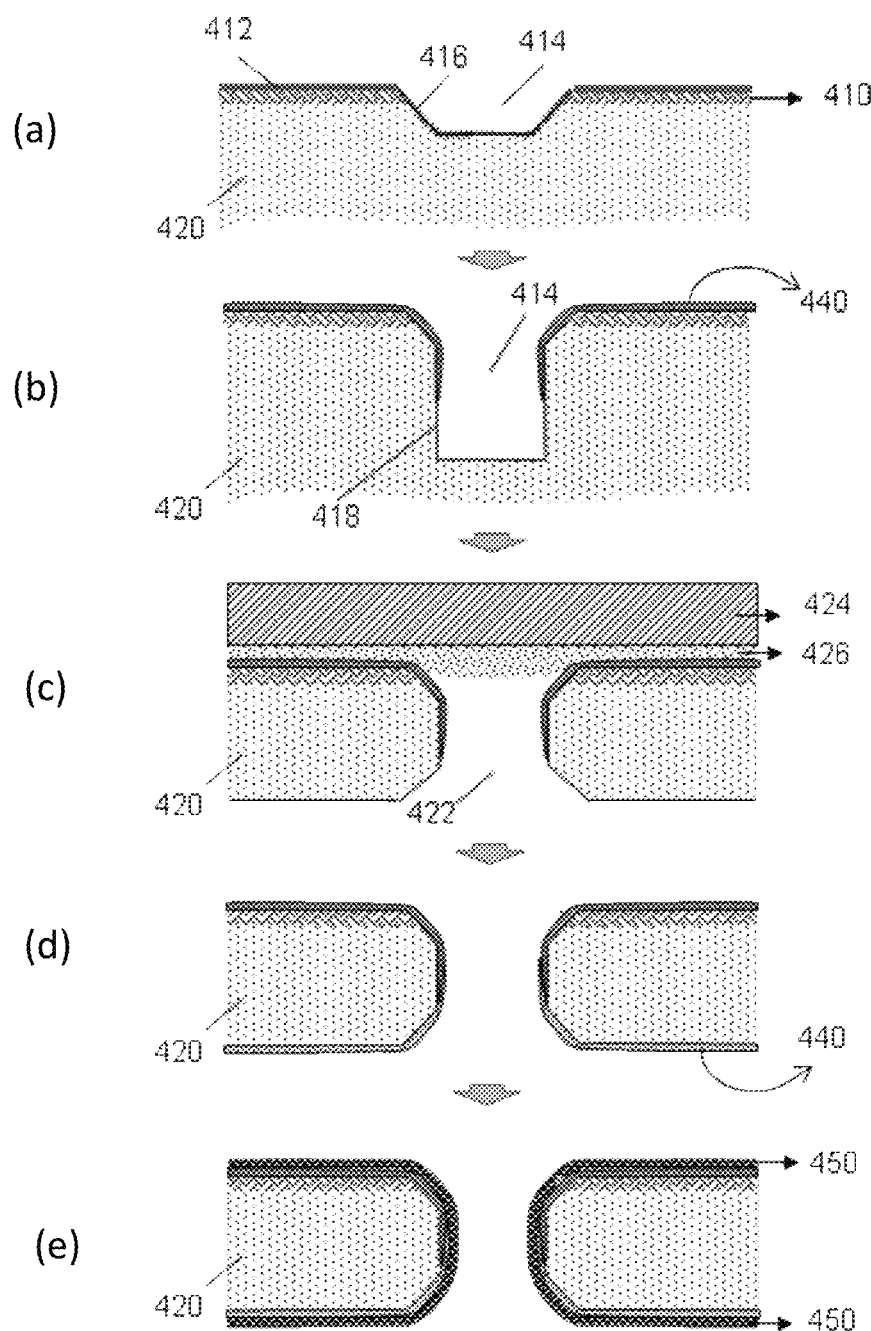
FIG. 3 illustrates different intermediate results of a packaging method according to one embodiment.

By way of illustration, an embodiment of an exemplary method for packaging will now be described with reference to FIG. 2, the present invention not being limited thereto. The packaging method 200 indicates standard and optional steps in the packaging method. Reference is also made to FIG. 3 illustrating different intermediate results as can be obtained using a packaging method as shown in FIG. 2.

In a first step 210, a device is obtained comprising at least one component 410 on a substrate 420. Obtaining such a device may be performed by either obtaining a ready made device or by processing a component 410 on the substrate 420. The component 410 may be any type of component as described above. The substrate 420 may be any type of substrate as described above. In the present example, the illustration is given for a die on a wafer. In advantageous embodiments, a substrate 420 comprising a plurality of components 410 positioned on that same substrate is obtained. The latter may allow applying at least part of the packaging method simultaneously to the plurality of components 410, thus resulting in a time efficient process. More particularly, a part of the encapsulation process then can be performed simultaneously for different components, resulting in a gain in time, cost and effort. In FIG. 3 the illustration is given for a substrate 420 comprising two components 410. Typically such components 410 may be spaced by a predetermined distance, which in the case of dies can be referred to as the scribe line.

In a second step 220 a component 410 on a first part of the substrate 420 is separated from the remainder part of the substrate 420 such that a sloped side wall is induced for the packaged device and in a third step 230 encapsulation of the separated component 410 on the first part of the substrate 420 is encapsulated. These steps may be performed using a plurality of sub-steps, the invention not being limited thereto and a number of these sub-steps being optional. These sub-steps will further be described in more detail.

In optional step 240, an optional protective coating 412 is applied to the surface of the substrate 420 whereon or wherein the component 410 is made. Application of a protective coating 412 may prevent the component 410 from becoming damaged during future steps in the processing. Such a protective coating 412 may for example be made from a passivating material, such as for example an oxide or nitride like TiN, TaN, $TiO_2$, a carbide such as SiC, a metal such as Ti, Ta. Also a multilayer could be used combining properties of different of these layers. The latter may result in an improved reliability. Whereas polymers typically may have a low density and therefore may act as a poorly reliable diffusion barrier or protection barrier, it could be used in combination with other layers.

In step 250, dicing of a recess 414 is performed in the surface of the substrate 420. The position of the recess 414 typically may correspond with a position of an edge of a packaged device. Therefore the position for forming the recess may be selected close to the position of the component, so that the volume of the packaged device can be kept small, or in between different components 410, if different components 410 are present on the same substrate 420. The dicing of the recess 414 in the present example is performed using a blade shaped so that a recess 414 with at least one sloped wall 416 (oriented non-perpendicular to the top substrate surface) is made. The blade shape therefore typically may have significantly sloped blade sides. The angle made by the blade sides may be for example between 45° and 60°, the present invention not being limited thereto.

Instead of dicing, also other physical techniques could be used for obtaining a recess with at least one sloped wall, so as for example laser cutting using a particular laser profile. The recess made in this and following step 260 advantageously does not extend through the whole substrate 420, so that the substrate 420 still is a single piece. In other words, for the present example, dicing is performed only partially so that recesses 414 are formed that do not run through the whole substrate 420 and so that the components are not fully separated from each other. The latter will assist in simultaneously applying a part of the encapsulation step for a plurality of components, if present on the substrate. Depending on the type of blade chosen (e.g. a symmetrical blade or not), one or two sloped walls 416 will be created for the recess 414. Applying a physical technique so that sloped surfaces 416 are obtained will allow creation of rounded corners or less sharp corners, which is advantageous for use in bio-medical applications. The result of this dicing step is shown by the recess 414 in FIG. 3 part (a)

In step 260, further creation of the recess is performed by dicing at the same position as in step 250 but using a blade inducing a recess with straight walls 418. Again, alternatively, other physical techniques also could be used. The resulting combination of the two dicing processes can be seen as the recess 414 in FIG. 3 part (b). The result of step 250 and 260 is a recess, also referred to as a trench wherein the top is wider than the bottom. It is to be noticed that in particular embodiments, the order of steps 250 and 260 can be interchanged, so that first the recess with substantially straight walls is made and thereafter the sloped walls are introduced in the recess. Furthermore, in some embodiments, where reduction of the sharpness of edges is only required at one side, the recess may run through the complete substrate. In the latter case no further dicing or separation will be required. One embodiment thus may be characterized by the fact that a recess or cut is formed by using a double physical process creating differently sloped walls, e.g. a double dicing or cutting technique whereby walls with different slopes are induced.

In step 270, surface damage advantageously may be removed. The latter may for example be performed using surface plasma treatment, including dry etching, although the invention is not limited thereto. Another example of a technique that could be used is wet etching.

In an additional step 280, the optionally applied protective topcoat 412 for protecting the component, in the present example die, is removed. The latter may for example be performed using dry or wet etching. An example of a topcoat material that can be used is photoresist, although the invention is not limited thereto.

In step 290, a first capping layer 440 may be applied to the top surface and at the walls in the recess 414. Due to the shape of the recess 414, step coverage by the capping layer is good. Consequently, even using standard deposition techniques and relatively low temperatures, a good and relatively homogeneous capping layer can be formed, which may, after it also has been applied to the back (see further), allow for a first complete sealing. Selection of the appropriate materials for obtaining good biocompatibility may also be performed. The capping layer 440 also may be selected so that it acts as a diffusion barrier. Whereas for sealing the whole device, it is required to have an overall coverage, in one embodiment sealing of the upper and side part of the device may be sufficient and no further first capping layer 440 may be applied. The applied first capping layer 440 is indicated in FIG. 3 part (b).

According to the present exemplary packaging method 200, the device is then fixed 300 on a carrier 424 using for example a layer of glue 426, as indicated in FIG. 3 part (c). In this way, the backside of the substrate becomes available for processing.

In step 305, thinning of the backside of the substrate is performed. Such thinning may for example be performed until a thickness of 80 μm, although the invention is not limited thereto. The thinning may be performed until the trenches, also referred to as recesses, are reached that are previously made at the front side of the substrate. In this way, different dies, if present on the substrate, are physically separated from each other. The previously formed recesses thus become cuts. The thinning may be performed using the conventional thinning processes.

In step 310, the edge may be provided with a sloped side wall. Advantageously, the latter may be performed simultaneously for different dies, using a technique rounding both edges of the cut simultaneously. The provision of sloped side walls will allow that also the corners at the edges on the backside of the substrate will be less sharp. The sloped side walls at the back may be made using a dicing technique with sloped blade, although the invention is not limited thereto. The sloped side walls may for example also be made using a physical technique for creating sloped side walls, or even a chemical etching technique for creating a sloped side wall, or other process. The result of the creation of the sloped side walls can be seen in FIG. 3 part (c).

Optionally remaining particles and/or the surface damage induced by the thinning process and by the technique used for creating sloped side walls may be removed, as shown in step 320, e.g. by surface plasma treatment. Such a step may have a cleaning effect, whereby all particles related to the wafer thinning and dicing are removed, and a smoothening effect, wherein any damage and roughness can be reduced or removed. Materials that could be used for this cleaning and/or smoothening step are for example HF, $HNO_3$, Acetic Acid, HCl, TMAH, KOH.

In case full encapsulation is envisaged, which may often be the case in bio-medical applications, the first capping layer 440 now optionally also may be applied to the bottom surface and the side walls previously being part of the recess. Again, in case rounded corners are provided, this may assist in obtaining a good step coverage. Application of the first capping layer 440 to the bottom side is indicate by step 330. In FIG. 3 part (d) the presence of the capping layer 440 is indicated.

In optional step 340, the carrier is removed, now resulting in one or more individually packaged devices separated from each other. The latter can also be seen in FIG. 3 part (d).

In optional step 350, cleaning of the component may be performed. Materials that could be used for this cleaning step are for example, water, IPA, NPA, Acetone, DMSO, NMP a mixture of SC1 and SC2, etc.

Techniques for performing cleaning or smoothening such as for example provided for in steps 320 and 350 may comprise batch processing or single wafer processing, dispensing of chemical through a puddle, spraying, high pressure nano spraying, such spraying assisted with ultrasonics, meganonics, etc.

In a further optional step 360, an additional encapsulation may be applied, e.g. by embedding the device in a silicone layer. Examples of bio compatible materials that can be used are Parylene, Hydrogels, etc. Materials that could be used preferably have a good biocompatibility, are soft, are flexible and are reliable. The encapsulation may be made as multilayer of different materials. For example, embodiments of the present invention not being limited thereby, the multilayer may comprise one layer having anti-inflammatory properties, e.g. a layer including anti-inflammatory drugs, one layer having the property of being soft, . . . . Such an additional encapsulation may result in a two-layer encapsulation that provides an hermetic encapsulation making the packaged device suitable for bio-medical applications. The resulting packaged device is shown in FIG. 3 part (e). Further encapsulation by applying additional layers also may be performed Whereas in the above exemplary method, the process is given for a particular shape of the blade, such shape may be adjusted. The selected shape of the blade and the corresponding recess made, may depend on the thickness of the substrate, the distance between neighboring components, if these are present, etc.

Figure 4:
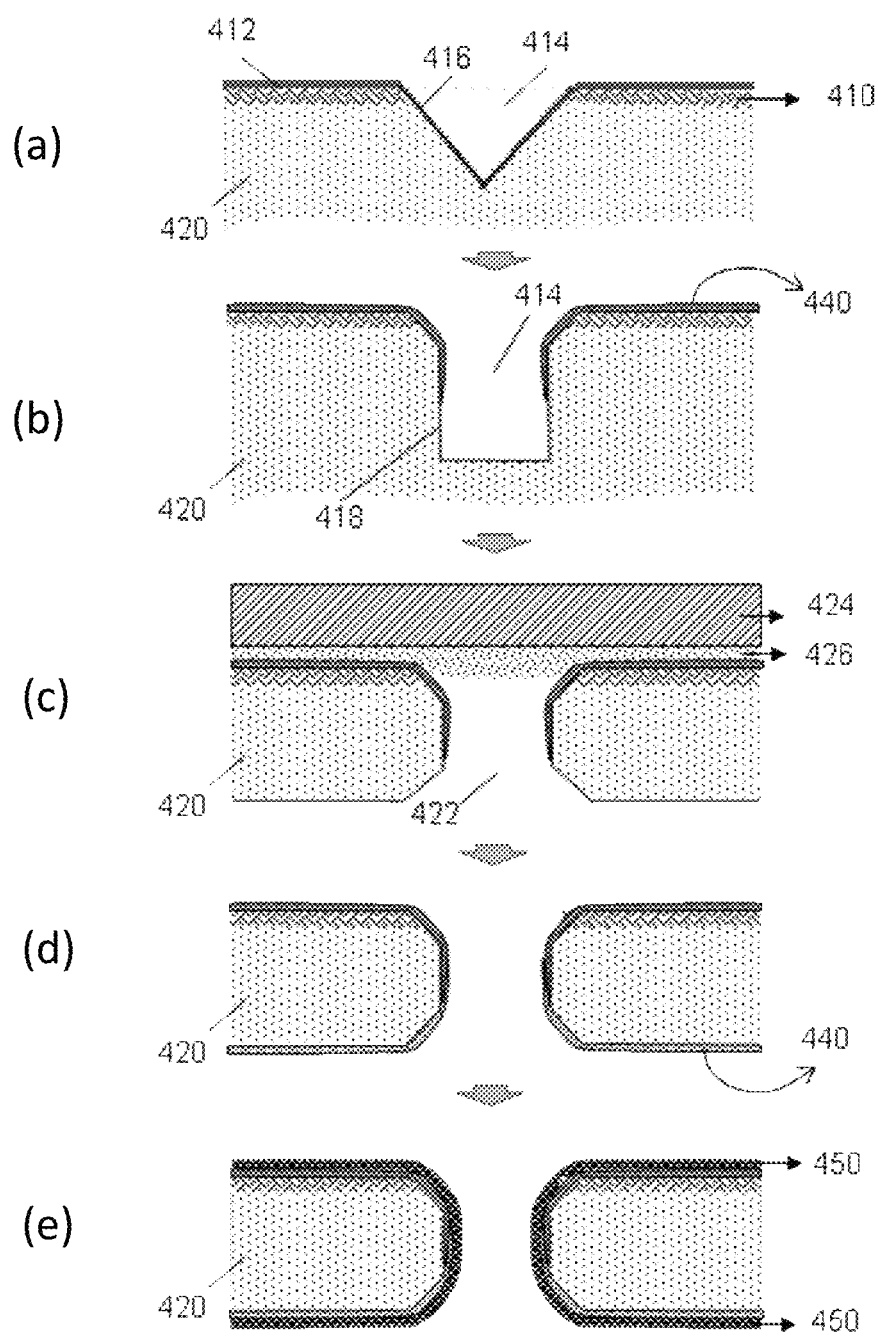
FIG. 4 illustrates different intermediate results of a packaging method according to one embodiment.
Figure 5A:
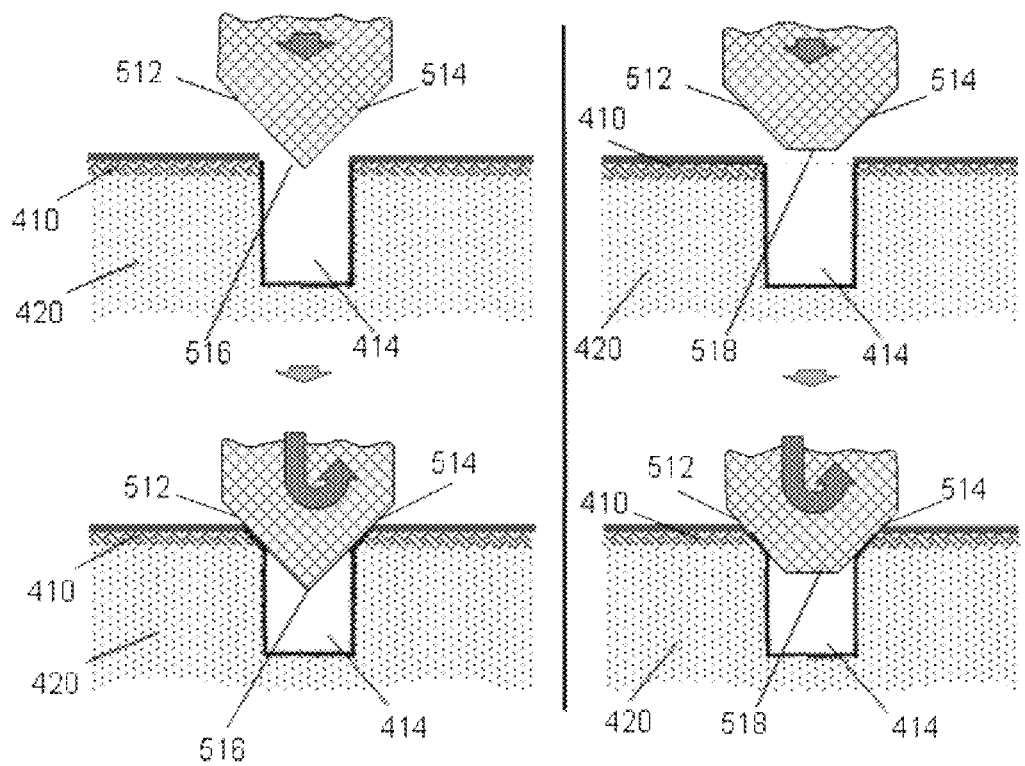
FIG. 5A illustrates the use of a differently shaped dicing blade and the corresponding intermediate results in a packaging method according to one embodiment.
Figure 5B:
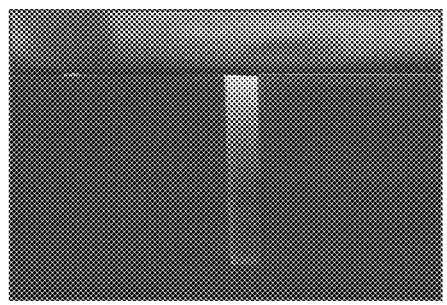
FIG. 5B illustrates scanning electron microscope images of cuts made with a straight blade, with a bevel blade and by combination of cutting with a straight and with a bevel blade, as can be used in one embodiment.
Figure 5B:
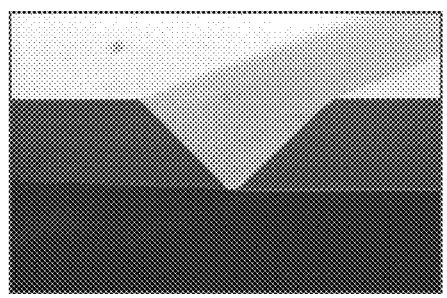
Figure 5B:
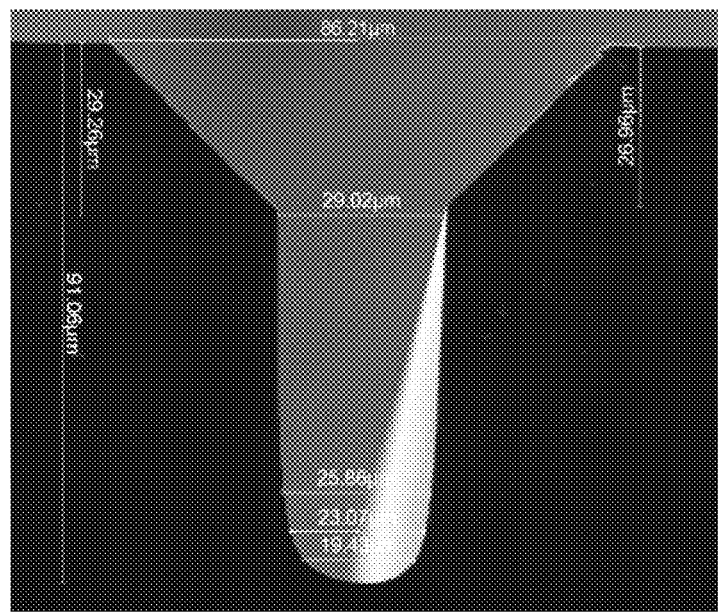

In a second particular example, a similar processing sequence as in the first particular example may be adapted, but the step or steps of dicing with a dicing blade inducing a recess with sloped surfaces may be performed with a blade having a different shape. Depending on the blade shape, the initial shape of the recess may be different. Whereas in the first particular example the initial blade had two sloped sides and a broad flat surface as blade edge, FIG. 4 illustrates a similar process wherein the blade has two sloped sides touching each other substantially at a line edge and having no additional flat surface. From the shape of the recess 414 it can be seen that the shape of the blade used for the initial dicing is different from the blade used in the example shown in FIG. 3. In FIG. 5A the effect of the two blade shapes is shown in more detail, FIG. 5A part (a) illustrating the situation for a blade having sloped blade sides 512, 514 reaching each other at an edge 516, and FIG. 5A part (b) illustrating the situation for a blade having an additional flat portion 518 at the cutting edge. The final shape of the recess, after combining the sloped surface dicing and straight dicing is the same. By way of illustration, scanning electron microscope images are shown in FIG. SB of a recess created with a straight blade (part (a)), a recess created with a bevel blade (part (b)) and a recess created by combining a cut with a straight blade and a cut with a bevel blade (part (c)). In one embodiment, the recess advantageously is obtained by first providing the cut with the straight blade and thereafter providing the cut with the bevel blade.

Figure 6A:
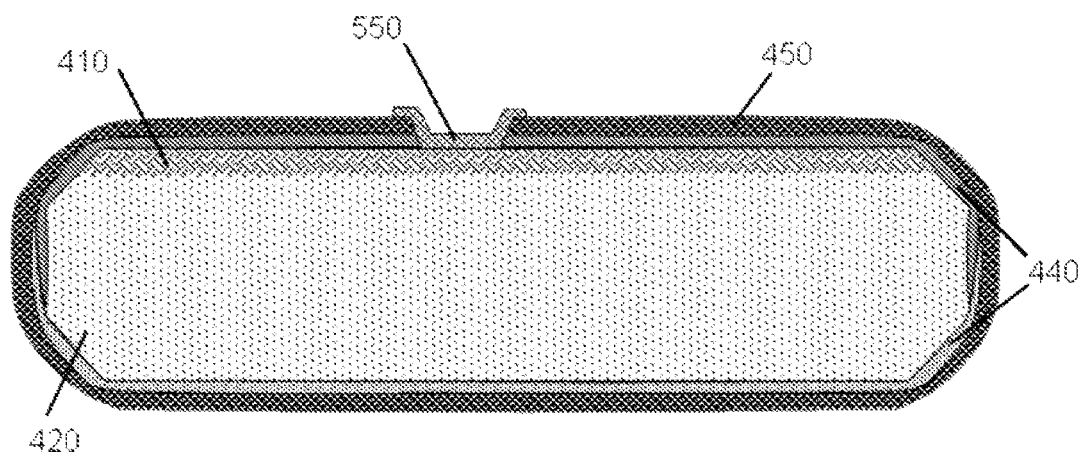
FIGS. 6A and 6B illustrate the result of a packaging method with additional feedthrough processing step, according to one embodiment.
Figure 6B:
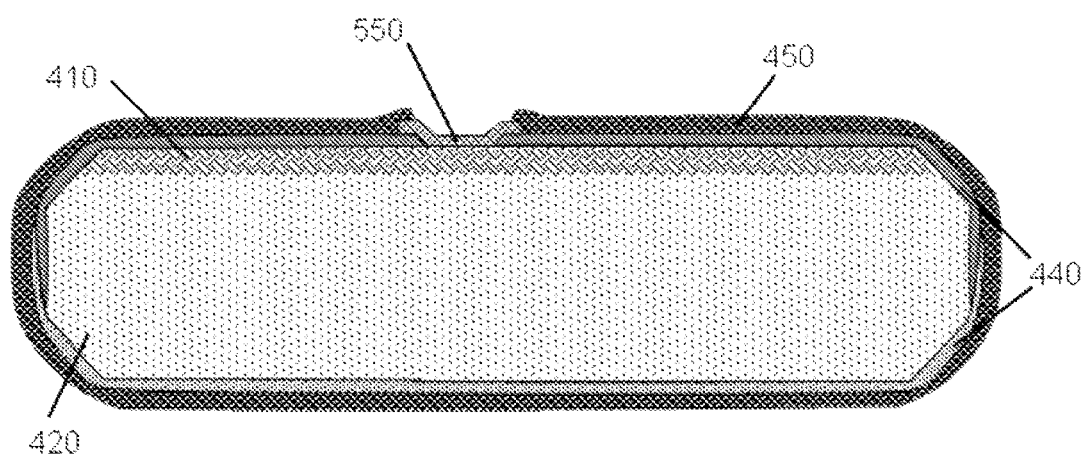

In one particular embodiment, the packaging method furthermore is adapted for providing feedthroughs to pass signals, data or materials to and from the component. Such feedthroughs may for example include electrodes to transfer electrical signals, although the invention is not limited thereto. FIGS. 6A and 6B illustrate examples of a feedthrough 550 for a packaged device according to one embodiment, in the present examples being an electrode for transferring electrical signals. The electrode 550 may be provided after the provision of the encapsulation 440, 450, e.g. by locally removing the encapsulation 440, 450 so that the surface of the component 410 is free and by providing the electrode 550 on the surface of the component 410 in any suitable way, e.g. by depositing a metal layer. An example thereof is shown in FIG. 6A. Alternatively, the electrode 550 also may be provided before or in between different steps of the packaging process so that the feedthrough 550, in the present example being an electrode, can be partially covered by an encapsulant 450. FIG. 6B illustrates an example whereby the component 410 on the substrate 420 is first covered by a capping layer 440, then, after local removal of the capping layer 440, the electrode 550 is provided and thereafter the encapsulation layer 450 is provided partially covering the electrode. The latter may for example be advantageous if free end portions of the electrode would result in unwanted electrical, chemical or physical behavior. Depending on the behavior envisaged for the feedthroughs 550, the most appropriate method for providing the electrode may be selected. Other feedthroughs that may be provided may for example be liquid feedthroughs for capturing liquids in a component acting as a microfluidic device. If the device or die is for example a MEMS device with a sensor that needs to be in direct contact with bodily fluids, the feedthrough may be just a hole and the sensor part may be made biocompatible, taking care on hermetic closure in itself. Another possibility is a device being or comprising a MEMS with membrane for pressure sensing. This membrane can be encapsulated if necessary for biocompatibility or hermeticity but care should be taken, since the encapsulation has to be done allowing reliable pressure sensing.

According to particular embodiments, the processing performed for packaging the device may be selected such that all processing is performed at temperatures below 400° C. Embodiments wherein rounded edges are induced in the device are especially suitable for low temperature processing as the step coverage when depositing a layer is inherently better.

In advantageous embodiments, the packaging/encapsulation processing is performed without leaving traces that are non-biotolerable. For example, the processing steps, more particularly those related to packaging/encapsulation may be selected such that no toxic solvents are used, no cupper Cu is used or no nickel Ni is used. So, whereas Cu can and typically will be used in CMOS processes itself, it is avoided in the packaging/encapsulation processes. In order to check biocompatibility, after separation and encapsulation of the dies, testing may be performed on biocompatibility.

It is an advantage of one embodiment that the method for packaging makes use of at least one physical process for the separating step. The packaging methods may be substantially independent on the materials used for the device, whereas for example when using etching different etch steps are required for different substrate materials. Application of a physical separation method is relatively fast resulting in an acceptable manufacturing time. Physical processes such as dicing are fast and cheap, resulting in an economically viable method. Furthermore, the physical processes used for separating are less complex compared to for example sloped etching.

In one embodiment, a method for packaging a chip is described whereby the method is characterized by the steps of obtaining a chip on a substrate and providing a hermetic bio-compatible packaging by providing a first capping layer and a further encapsulation layer in solid contact with the chip integrated on the substrate. Although advantageous for obtaining good step coverage and therefore for having an improved encapturing reliability, the creation of sloped edges for the device during separation is not strictly required. Other features and advantageous for using stacked layer encapsulation can be seen in the embodiments described above.

Figure 7:
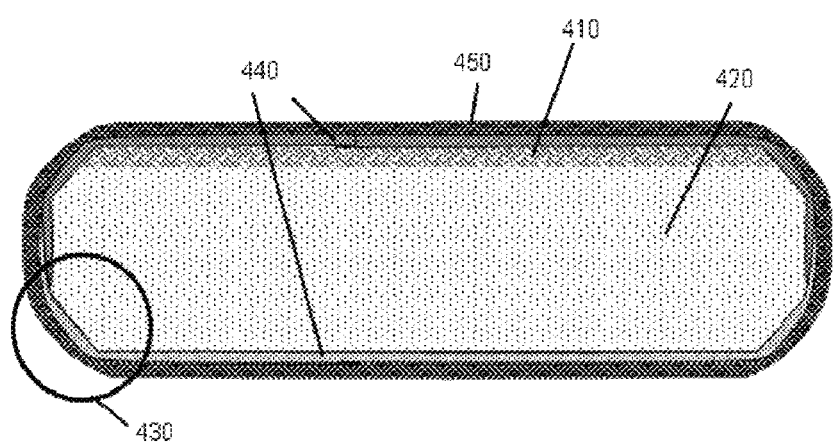
FIG. 7 illustrates an example of a packaged device according to one embodiment.

In a second aspect, there is a packaged device for bio-medical applications. The device may be an integrated circuit, MEMS or other device, as also indicated in the description of the first aspect. In one embodiment, there is a device for biomedical applications comprising a component provided on a substrate and at least one sloped side wall induced using a physical process. Such sloped side wall of the device may enhance step coverage of a capping layer applied for encapsulation, avoid injury or damage, etc. In another embodiment, there is a device for bio-medical applications comprising a component provided on a substrate and having a hermetic bio-compatible packaging comprising a capping layer, being a first encapsulation and typically being a biocompatible layer also acting as diffusion barrier, and an encapsulation layer, being a second encapsulation. Such encapsulation, which typically may be provided in solid contact with the component and/or substrate e.g. be deposited on the component and the substrate, may ensure good biocompatibility of the packaged device during and after implantation. In still a further embodiment, there is a packaged device for use in bio-medical application, the packaged device being biocompatible and the packaged device comprising a combination of features of the first particular embodiment of the second aspect and features of the second particular embodiment of the first aspect. By way of illustration, the present invention not being limited thereto, an example of a biocompatible device is shown in FIG. 7, illustrating standard and optional features of the packaged biocompatible device. The biocompatible device comprises a component 410 and a substrate 420, which may be similar to those parts as described above and in the first aspect. The device furthermore comprises at least one sloped side wall 430, which also may be referred to as a rounded edge. Advantageously, such sloped side walls 430 or rounded edges may be present at a plurality of edges or even at each edge of the packaged device 400. The sloped side walls 430 or rounded edges 430 may be made using a method as described in the first inventive aspect, although the invention is not limited thereto. Such sloped side walls 430 or rounded edges may enhance step coverage for a capping layer 440 that may be present. It may assist in avoiding damage of an encapsulation material 450 that may be present or assist in avoiding injury of tissue after implantation. As indicated the component and substrate may be encapsulated with a first encapsulation being a biocompatible capping layer 440 or biocompatible capping layers 440. These advantageously may have the function of a diffusion barrier, preventing diffusion from elements from the device into the body where the device is implanted and/or preventing diffusion from elements from the body into the device, which may result in malfunctioning. Layers that can be used as capping layers may be selected based on their biocompatibility. As indicated above the rounded corners may assist in obtaining a good coverage. It is to be noticed for some applications that the capping layer does not need to be present at all sides of the device, whereas for other applications e.g. for some bio-medical applications full hermetic encapsulation is required and obtained with the stacked layer encapsulation. The materials that may be used as capping materials may be silicon oxide, silicon nitride, bio compatible polymers, etc. Advantageously multilayers can be used combining properties of several layers. As indicated advantageously also a second encapsulation material 450 may be present. Such an encapsulation material 450 may be an embedding in for example silicone, Examples of bio compatible materials that can be used are Parylene, Hydrogels, etc. Materials that could be used preferably have a good biocompatibility, are soft, are flexible and are reliable. The encapsulation may be made as multilayer of different materials, as also described above. As discussed above for the packaging method, additional feedthroughs for passing data or materials also may be provided. In case feedthroughs for passing electrical signals are provided, such feedthroughs may be electrodes made of biocompatible conductive materials such as for example inert metals, Ti, Ta, Pt, Au, IrO2, PEDOT.

Figure 8:
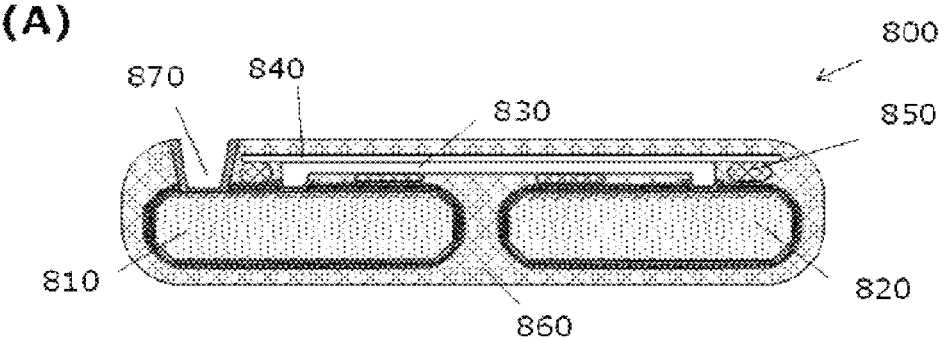
FIG. 8 to FIG. 10 illustrate different hermetic implantable systems comprising different packaged devices, according to one embodiment.
Figure 8:
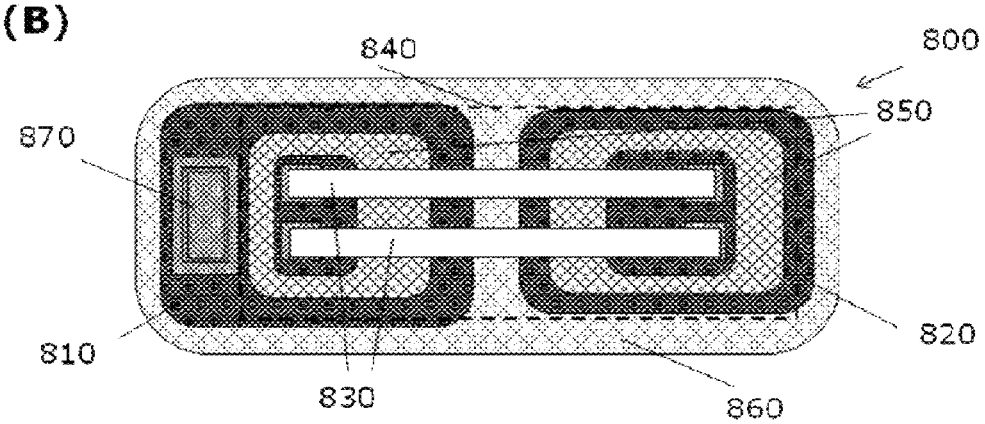
Figure 9:
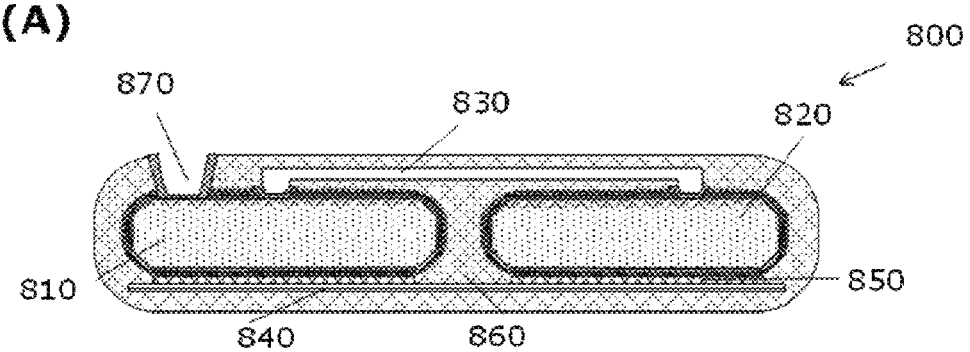
Figure 9:
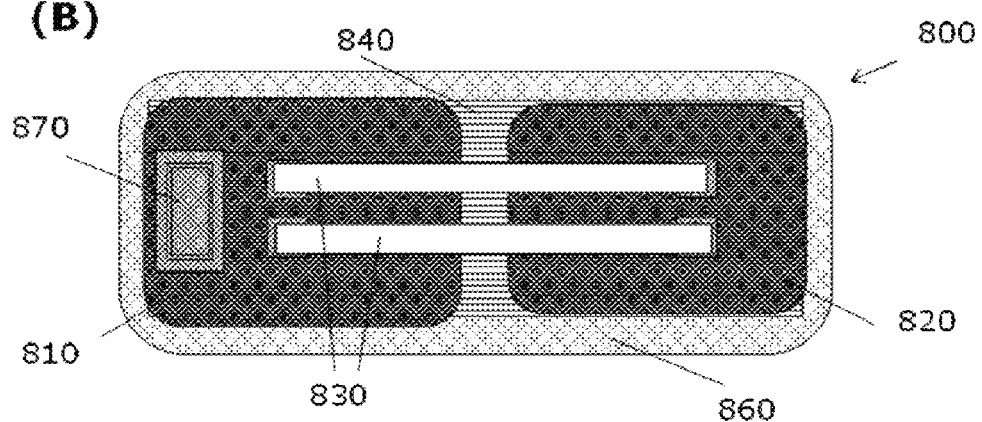
Figure 10:
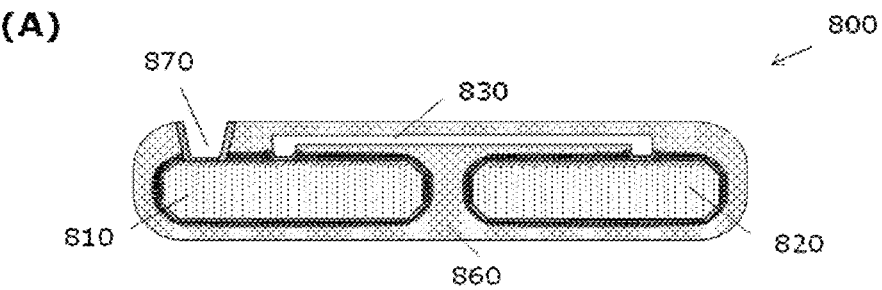
Figure 10:
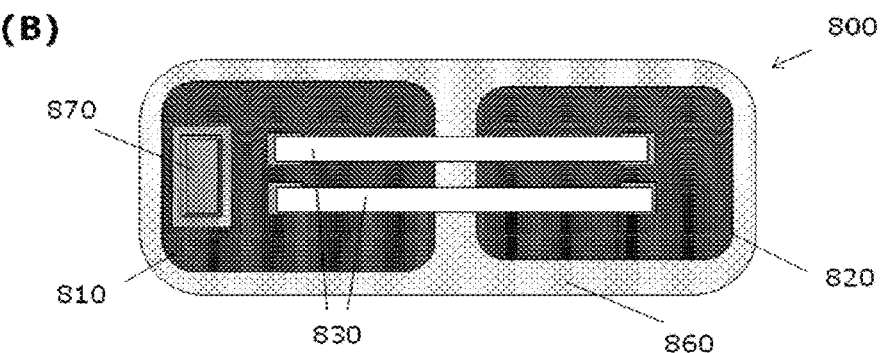

In a third aspect, there is an implantable system, the implantable system comprising at least one implantable device according to one embodiment. The at least one implantable device may be a combination of different heterogen dies, advantageously packaged using a method as described above. Examples of such combinations may be CMOS logics (such as steering, programmable devices, . . . ), MEMS (such as membranes for example for pressure sensing, drug reservoirs, microfluidics for drug delivery, . . . ), battery, antenna (for example for loading a rechargeable battery, for programming a reprogrammable steering. Any combination or subset of the mentioned dies can be used. Part of the dies or all dies can be encapsulated in one package. Different dies may be electrically connected via inter-die-metallization, whereby the inter-die-metallization can be included in the package. In case a flexible package is used, the inter-die-metallization is preferably stretchable. This can for example be obtained by shaping the metallization as a sine wave or horse shoe. Typical materials that can be used for the inter-die-metallization is gold or platinum, although the invention is not limited thereto and all, preferably biocompatible, conducting materials may be used. The overall system furthermore comprises a global packaging, encapsulating the different components of the system. Such global packaging or encapsulation may be applied using a wafer-level technique e.g. as described above, or may be applied using another technique, such as e.g. via injection molding. By way of illustration, the present invention not being limited thereto, some examples of implantable systems are illustrated in FIG. 8 to FIG. 10. FIG. 8 illustrates a cross-sectional view (A) and a top view (B) of an implantable system 800 comprising two packaged dies 810, 820 according to embodiments of the second aspect electrically interconnected via an inter-die-metallization 830, in the present example being a set of two metal connections. The dies and the metallization are supported using a flexible or stretchable support 840 to which the packaged dies 810, 820 are bonded via a bonding 850. A global encapsulation, 860 encapsulates the different components to safeguard the biocompatibility of the system 800. The system 800 can be provided with a global feedthrough 870, which may be an electrical feedthrough, fluid feedthrough, etc. comparable to the feedthroughs as described above for the packaged devices. FIG. 9 illustrates an example of a similar structure, whereby the support 840 is only provided for supporting the dies 810, 820 and not the metallization. In FIG. 10 a configuration without support 840 is shown. It will be appreciated by the person skilled in the art that the systems as shown in FIG. 8 to FIG. 10 are only examples of a plurality of different configurations of implantable systems encompassed within the scope of embodiments of the present invention.

Figure 11:
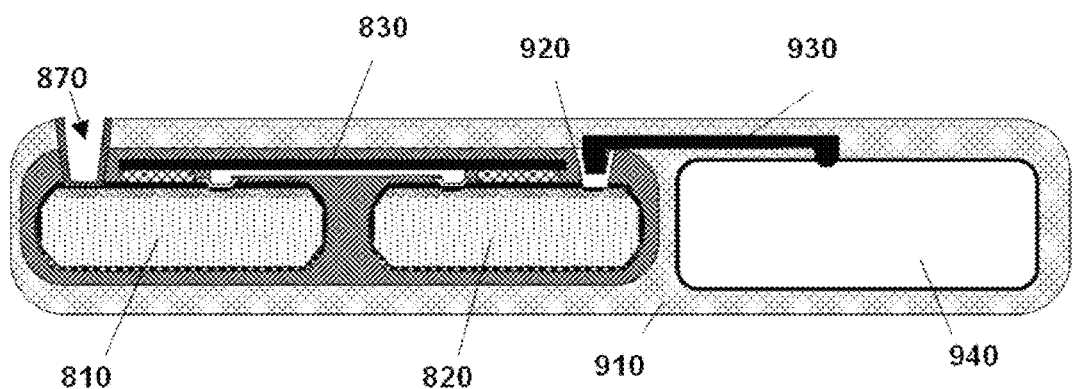
FIG. 11 illustrates a hermetic implantable system with further embedding, according to one embodiment.

Whereas in the examples of FIG. 8 to FIG. 10 a global biocompatible encapsulation is provided wherein only electronics and metallization is embedded, optionally also further encapsulation may be applied. For example, in case the total system is not only composed of dies, e.g. silicon based chips, and interconnects, but also contains other subparts such as for example a battery or passives, a further embedding can be applied, as shown in FIG. 11. In the present example, applying a further global embedding 910 can be carried out with or without the use of a flexible substrate, depending on the particular implantable device. The further embedding 910 can provide additional support for a multitude of sub-devices. Via a feed through 920 an intermetallization 930 to connect the electronic subparts with the other parts 940 can be performed. The interconnect pitch may typically be larger. Consequently, board level embedding techniques can be selected for the fabrication step, whereas for a first global encapsulation both board level and wafer level embedding technologies may be considered, since smaller metallization pitches will be envisaged for the first global encapsulation. It is to be noticed that such an additional global embedding can be performed outside a clean room. In some embodiments, thus global embedding may first be done at the level of some electronics components and metallization with a first embedding layer, in an interposer-like package, and further embedding may be performed for further enclosing other components such as for example a battery.

It is an advantage of one embodiment that packaging can be performed in two phases, a first whereby encapsulation is performed for generating a diffusion barrier and for creation of feedthroughs and a second phase, wherein global interconnecting and embedding is performed. The last phase can provide mechanical support of the system, electrical interconnections between dies, creation of functional feedthroughs, etc.

Figure 12:
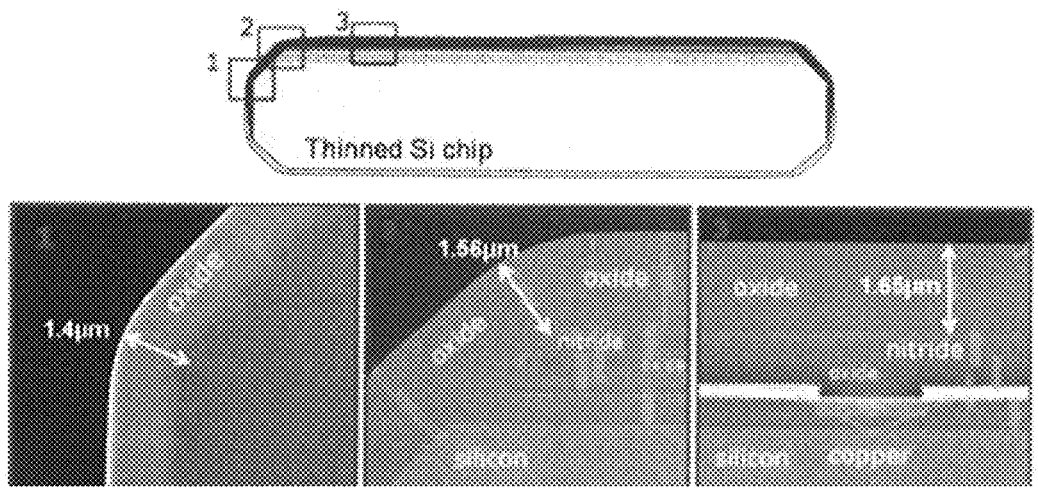
FIG. 12 illustrates SEM pictures illustrating step coverage as can be obtained using a method according to one embodiment.

By way of illustration, embodiments of the present invention not being limited thereby, an example of a step coverage that can be obtained for an encapsulated device encapsulated via a method as described above is shown in FIG. 12 and discussed below. The embedding uses a passivation stack of 50 nm SiC, 400 nm oxide and 500 nm Si-nitride. A further top encapsulation layer of silicon oxide was selected. The oxide encapsulation at the top had a total thickness of 1.5 µm. One technique applied in the present example to further strengthen the hermeticity after encapsulation is the provision of the encapsulation by depositing the encapsulation layer in a two-step process. Instead of depositing a single layer with thickness of 1.5 µm, the encapsulation layer is built up from 2 oxide layers, in the present example each being about 0.8 µm thick and deposited immediately after each other. By fabricating the oxide encapsulation as a two-layer stack, the influence of an occasional pinhole on later diffusion is reduced, as it is unlikely that pinholes in two different layers will occur at the same location. This principle can be applied to certain embodiments and is not limited to the present example. The device was also encapsulated at a bottom side, whereby the bottom encapsulation existed from a stack of two oxide layers having a total thickness of 1.5 µm and whereby no passivation stack was present. The latter typically may be left out since the bottom side of the dies contain no patterns of Cu or other harmful materials. As is understood, the external chip electrodes typically are fabricated in a biocompatible material since these are not covered by a diffusion barrier.

Figure 13:
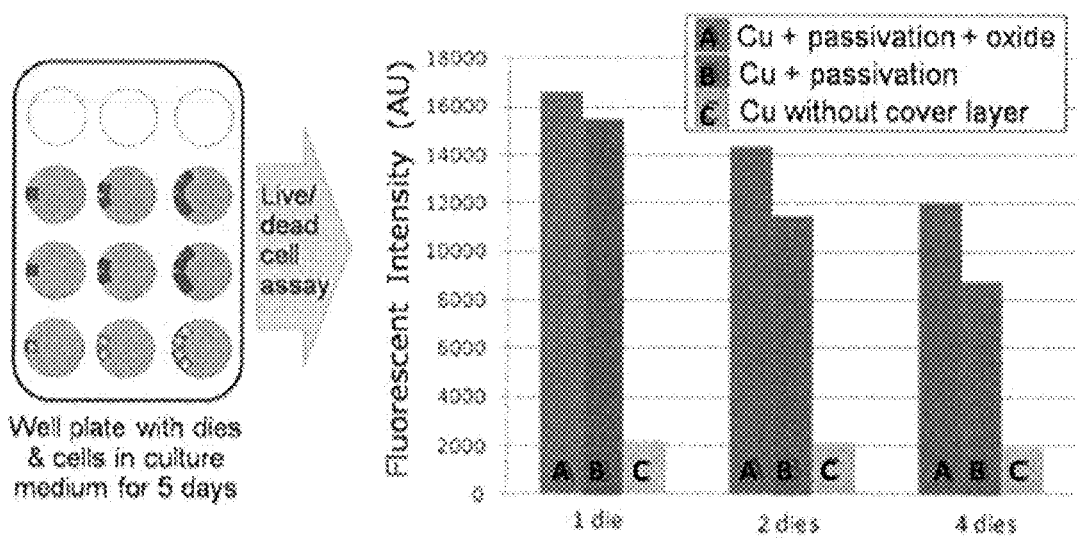
FIG. 13 illustrates biocompatibility tests for packaged components illustrating features and advantages of one embodiment.

By way of illustration, the functionality of the encapsulation technique as diffusion barrier is tested. One test illustrating the diffusion barrier properties relates to encapsulation of silicon dies prepared with Cu patterns on the topside, using a conventional damascene process. The dies are rounded using a method according to one embodiment. The top encapsulation used was as described in the exemplary structure above. In order to test the encapsulation and biocompatibility, cell culture tests were carried out, using neonatal rat cardiomyocytes as test cells. In a well plate, culture medium and cells were brought into contact with 3 types of chips: an encapsulated chip as described above whereby Cu patterns are covered with a passivation layer stack and an encapsulation layer, referred to as tests A, chips whereby only a passivation layer on top of the Cu is present, referred to as tests B, and chips without covering layer, i.e. whereby the Cu patterns are uncovered, referred to as tests C. The wells had 1, 2 or 4 dies of each type of chips, all chips being 5×5 mm$^2$. After a co-culture of 5 days, a live-dead cell assay was applied and the fluorescent intensity of each well was measured, as shown in FIG. 13. Since only cells which are alive are fluorescent, the determined intensity was a figure of merit for the amount of living cells. Taking into account that Cu is poisonous, it can be seen that passivation already blocks the Cu diffusion already quite well, while the gain is even larger when also an oxide encapsulation was applied. The latter illustrates that good biocompatible packaged devices can be obtained.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. An implantable bio-medical device, the device comprising a component present on a substrate, the component and the substrate hermetically sealed within an encapsulation, the encapsulation comprising a continuous layer of biocompatible material around all outer surfaces of the component and the substrate, the substrate comprising at least one sloped side wall between a top surface and a bottom surface of the substrate, wherein the continuous layer of bio-compatible material around all outer surfaces of the component and the substrate comprises a bi-directional diffusion barrier whereby no element from the device diffuses into a site of implantation and no element from the site of implantation diffuses into the device.

2. The device of claim 1, wherein the at least one sloped side wall is oriented non-perpendicular to the top surface of the substrate.

3. The device of claim 1, wherein the substrate comprises a sloped side wall at each corner of the substrate such that all corners of the implantable bio-medical device are rounded.

4. The device of claim 1, wherein the component comprises one of an integrated circuit, an actuator, a sensor, a microfluidic device, and a battery.

5. A hermetic implantable system comprising at least two implantable bio-medical devices according to claim 1 encapsulated within a global biocompatible encapsulation layer.

6. A hermetically encapsulated biocompatible device for bio-medical applications, the device comprising a component on a substrate, the component and the substrate hermetically sealed within an encapsulation around all outer surfaces of the component and the substrate, the encapsulation comprising stacked layers fully encapsulating the device, at least one of the layers being formed of a bio-compatible material, the substrate comprising at least one rounded edge between a top surface and a bottom surface of the substrate.

7. The device of claim 6, wherein the at least one rounded edge comprises a sloped side wall that is oriented non-perpendicular to the top surface of the substrate.

8. The device of claim 6, wherein the encapsulation comprises a capping layer of bio-compatible material.

9. The device of claim 8, wherein the capping layer comprises a bi-directional diffusion barrier.

10. The device of claim 8, wherein the encapsulation further comprises a second layer over the capping layer.

11. The device of claim 10, wherein the second layer comprises silicone.

12. The device of claim 6, further comprising a membrane configured to sense pressure.

* * * * *